May 31, 1966 | E. S. BOERNER | Plant Pat. 2,638
CHRYSANTHEMUM PLANT
Filed June 7, 1965
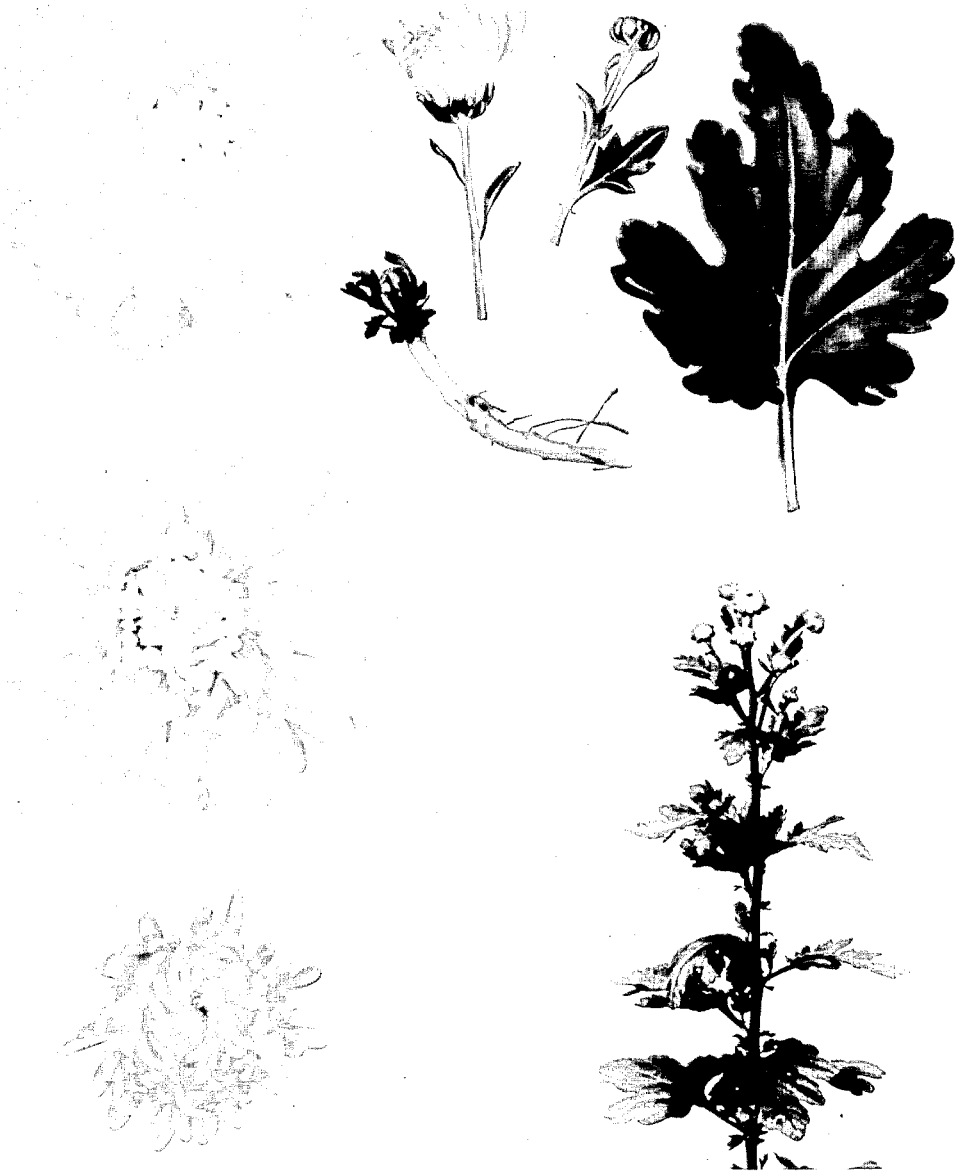
Inventor.
E. S. Boerner
By: Robb & Robb
Attorneys.

United States Patent Office

Plant Pat. 2,638
Patented May 31, 1966

2,638
CHRYSANTHEMUM PLANT

Eugene S. Boerner, Newark, N.Y., assignor to Jackson & Perkins Company, Newark, N.Y., a corporation of New York Filed June 7, 1965, Ser. No. 462,153
1 Claim. (Cl. Plt.—78)

The present invention relates to a new and distinct variety of chrysanthemum plant of the incurved class, which was originated by me by crossing an unnamed and unpatented seedling of "Sandpiper" (Plant Patent No. 1,932) × "Titmouse" (Plant Patent No. 1,630) with the variety "Sandpiper."

The primary objective of this breeding was to produce a new chrysanthemum variety having the early blooming habit and the flower color variations of the variety "Sandpiper," combined with the incurved flower petal tendencies of the variety "Titmouse." This objective was fully achieved along with other desirable improvements, as evidenced by the following unique combination of characteristics which are outstanding in the new variety and distinguish it from its parents, as well as from all other varieties of which I am aware:

(1) An upright habit of plant growth;
(2) Large foliage;
(3) An early blooming habit;
(4) Flower petals of incurved form; and
(5) A distinctive and attractive general tonality of the flowers corresponding to Lemon Chrome, very lightly overcast with Apricot Yellow.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—An unnamed seeding of "Sandpiper" × "Titmouse."
*Pollen parent.*—"Sandpiper."
Classification: Incurved:
Growth: Free; upright.

Locations where observations made: Outdoors at Newark, New York, in the early morning during the early part of the month of October.
Cold resistance: Winter hardy in northern New York State.
Blooming period: In Newark, New York climatic area, blooms begin in September and continue until frost.

*Flower*

Bud:
*Color.*—When petals first divide—Orange Chrome, Plate 2. When petals begin to unfurl—Orange-Buff, Plate 3. When half-blown:—Inside—Scarlet, Plate 1, lightly overcast with Cadmium Yellow, Plate 3; outside—Deep Chrome, Plate 3.
*Peduncle.*—Color—Mignonette Green, Plate 31. Strength—strong.

Bloom:
*Size.*—From 5½–6 inches.
*Stem.*—Strong.
*Form.*—Incurved.
*Petalage.*—Oval.
*Color.*—Center of flower—Apricot Yellow, Plate 4, lightly overcast with Deep Chrome, Plate 3. Outer petals—Lemon-Chrome, Plate 4. Base of petals—Lumiere Green, Plate 17. Inside of petals—Lemon-Chrome, Plate 4, very lightly overcast with Apricot Yellow, Plate 4. Reverse of petal—Pinard Yellow, Plate 4, lightly overcast with Empire Yellow, Plate 4.
*Petals.*—Texture—medium thick. Form—oval.
*Fragrance.*—Characteristic chrysanthemum.

*Plant*

Form: Upright.
Growth: Strong.
Foliage:
*Size.*—Very large.
*Quantity.*—Abundant.
*Color.*—Upper side—Cress Green, Plate 31. Reverse side—Chromium Green, Plate 32.
*Texture.*—Leathery.

I claim:

A new and distinct variety of crysanthemum plant of the incurved class, substantially as herein shown and described, characterized particularly as to novelty by the unique combination of an upright habit of plant growth, large foliage, an early blooming habit, flower petals of incurved form, and a distinctive and attractive general tonality of the flowers corresponding to Lemon Chrome, very lightly overcast with Apricot Yellow.

No references cited.

ABRAHAM G. STONE, *Primary Examiner.*